United States Patent
Schröer

(10) Patent No.: US 6,486,345 B1
(45) Date of Patent: Nov. 26, 2002

(54) METHOD FOR PRODUCING 6,6-DIALKOXY-5-HYDROXY-3-OXO-HEXANOIC ACID ESTERS

(75) Inventor: Josef Schröer, Bottmingen (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/787,419

(22) PCT Filed: Sep. 23, 1999

(86) PCT No.: PCT/EP99/07100

§ 371 (c)(1),
(2), (4) Date: Jun. 11, 2001

(87) PCT Pub. No.: WO00/18718

PCT Pub. Date: Apr. 6, 2000

Related U.S. Application Data

(60) Provisional application No. 60/147,041, filed on Aug. 3, 1999.

(30) Foreign Application Priority Data

Sep. 25, 1998 (EP) .............................. 98118191

(51) Int. Cl.[7] .............................................. C07C 69/66
(52) U.S. Cl. ....................................... 560/174; 560/178
(58) Field of Search ............................... 560/174, 178, 560/179, 187

(56) References Cited

U.S. PATENT DOCUMENTS 5,347,039 A    9/1994   Leon et al. .................... 560/60

FOREIGN PATENT DOCUMENTS

EP    WO 92/10461    6/1992    ........... C07C/67/31
EP    WO 92/10503    6/1992    ............. C07F/7/18

OTHER PUBLICATIONS

Feryan Ahmed et al, "Convergent Synthesis of the C31–C46 Domain of the Phorboxazole Natural Products", Tet. Lett., vol. 39 (1998), pp. 183–186.*

Carlo Bonini et al, "Enzyme Catalysed Lactonization of 3,5 Dihydroxy Esters: Enatioselective Synthesis of Naturally Ocurring 3–Hydroxy–5–decanolide, (−)–Massoialactone, and 3–Hydroxy–5–icosanolide", Tet. Asymm., vol. 3 (1992), pp. 29–32.*

Yoo Tanabe et al, "A Novel and Efficient Synthesis of 2(5H)–Furanone Derivatives", J. Org. Chem., vol. 53 (1988), pp. 1560–1563.*

K.K. Sharma & K.B.G. Torssell, Synthesis and Cyclopentenones, Nov. 14, 1983, vol. 4, No. 6, pp. 1085 to 1089.

The Chemical Society of Japan, S. Kanemasa, N. Nakagawa, H. Suga & O. Tsuge,, Acid–Catalyzed Formation of γ–Oxo Esters from α–Hydroxy–γ–oxo Acetals, vol. 62, No. 1, pp 180 to 184.

* cited by examiner

*Primary Examiner*—Paul J. Killos

(57) ABSTRACT

A method for producing 6,6-dialkoxy-5-hydroxy-3-oxo-hexanoic acid esters of general formula (I), wherein the dianion of an acetoacetic acid alkyl ester is reacted with an aldehyde. The 6,6-dialkoxy-5-hydroxy-3-oxo-hexanoic acid esters of general formula (I) are important synthesis building blocks for producing HMG-CoA-reductase-inhibitors.

6 Claims, No Drawings

US 6,486,345 B1

METHOD FOR PRODUCING 6,6-DIALKOXY-5-HYDROXY-3-OXO-HEXANOIC ACID ESTERS

This application is a 37 national stage application of PCT/EP99/07100, filed on Sep. 23, 1999, which has benefit of priority of European Application 98118191.0, filed on Sep. 25, 1998, and which benefit of U.S. Provisional Application No. 60/147,041, filed on Aug. 3, 1999, which has benefit of priority of European Application 98119191.0, filed on Sep. 25, 1998.

BACKGROUND OF THE INVENTION

1. Field of the Invention

The invention relates to a process for preparing 6,6-dialkoxy-5-hydroxy-3-oxohexanoic acid esters of the general formula

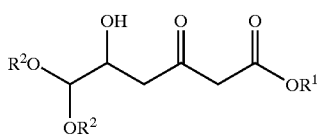

I in which $R^1$ and $R^2$ are identical or different and are $C_{1-6}$-alkyl.

2. Background Art

The abovementioned compounds are important synthesis building blocks for preparing numerous HMG-CoA reductase inhibitors (WO-A 92/10503).

According to WO-A 92/10503, these compounds are obtained by reacting an acetic acid ester with a γ-dialkoxy-β-hydroxy ester. However, this synthesis has the disadvantage that the latter starting material is difficult to obtain and therefore expensive.

BROAD DESCRIPTION OF THE INVENTION

It was the object of the invention to develop a simpler and more cost-effective route to the abovementioned synthesis building blocks.

This object could be achieved by the process according to the invention.

According to the invention, this involves reacting an alkyl acetoacetate of the general formula

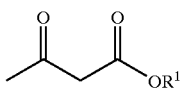

II in which $R^1$ is as defined above in the presence of a base with an aldehyde of the formula

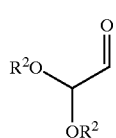

III in which $R^2$ is as defined above.

DETAILED DESCRIPTION OF THE INVENTION

A $C_{1-6}$-alkyl group is hereinbelow understood as a linear or branched alkyl group with 1 to 6 carbon atoms, namely methyl, ethyl, isopropyl, n-propyl, n-butyl, isobutyl, tert-butyl, pentyl and its isomers and hexyl and its isomers. Preference is given to the $C_{1-4}$-alkyl groups mentioned by name.

The process according to the invention has the advantage that the acetoacetic esters of the general formula II are available industrially.

Acetoacetic esters of the general formula II are obtained by reacting diketenes with the appropriate alcohol. The acetoacetic ester of the formula II may also be provided in situ, starting from diketene. Preferred acetoacetic esters of the general formula II are the methyl ester, the ethyl ester, the n-propyl ester, the isopropyl ester, the n-butyl ester, the isobutyl ester and the tert-butyl ester, particularly preferably the tert-butyl ester.

The aldehydes of the general formula III are generally commercially available. The preferred aldehyde of the formula III is glyoxal 1,1-dimethyl acetal.

The process according to the invention is advantageously carried out in an organic solvent in the substantial absence of water. Suitable solvents are ethers, such as, tetrahydrofuran, dioxane, diethyl ether, tert-butyl methyl ether, etc., aromatic compounds, such as benzene or toluene, or hydrocarbons, such as hexane, and mixtures of the abovementioned solvents.

The reaction temperature is generally chosen in a range from −80° C. to 130° C., preferably in a range from −40° C. to 20° C.

A base is used with the aim of forming the dianion of the alkyl acetoacetate of the general formula II. In principle, this dianion formation can be carried out directly using a strong base, such as, butyllithium, methyllithium, phenyllithium or sodium amide, lithium diisopropylamide or lithium hexamethyldisilazane.

In general, a two-step process is employed, by initially deprotonating the —$CH_2$— function using a relatively weak and also cost-effective base, and carrying out the dianion formation only in the second step using the abovementioned strong base. Suitable relatively weak bases are metal hydrides, such as, alkali metal hydrides and alkaline earth metal hydrides, preferably sodium hydride, but also secondary amines (preferably pyrrolidine), which forms an enamine as anion equivalent with the acetoacetic ester. In the latter case, the dianion is understood as the anion of the corresponding enamine.

The desired 6,6-dialkoxy-5-hydroxy-3-oxohexanoic acid ester can be obtained in a manner familiar to the person skilled in the art, for example by neutralization of the reaction mixture and subsequent extraction with a suitable solvent.

EXAMPLE 1

Preparation of 6,6-Dimethoxy-5-hydroxy-3-oxo-tert-butyl Hexanoate

At 0° C., 0.88 g (22 mmol) of sodium hydride (55–60% in mineral oil) in 50 ml of tetrahydrofuran was initially charged in a 250 ml round-bottomed flask. Using a syringe, 3.16 g (20 mmol) of tert-butyl acetoacetate were subsequently added to the sodium hydride suspension over a period of 5–10 min (evolution of hydrogen). Stirring was continued for 5 min, and 13.1 ml of n-BuLi solution (1.6 M in hexane) were then added dropwise to the reaction mixture at 0° C. over a period of approximately 10 min. Stirring was continued for about 1 h, and 5.7 g (22 mmol) of glyoxal 1,1-dimethyl acetal solution were subsequently added dropwise to the reaction mixture over a period of 5 min. Stirring was continued at 0° C. for 3 h. At 0° C., the reaction was quenched using 5 ml of concentrated HCl (>pH 8). The mixture was diluted with 30 ml of water and extracted twice with in each case 50 ml of diethyl ether. The crude product obtained by concentrating the organic phases was purified by column chromatography. In this manner, the desired compound was isolated in the form of a slightly viscous, slightly yellowish oil.

(Yield: 11%)

$^1$H NMR (400 MHz, CDCl$_3$): 1.47 (s, 9H)

2.73 (dd, 1H), 2.75 (brd. s, 1H), 2.82 (dd, 1H), 3.41 (s, 2H), 3.4–4(s, 3H), 3.45 (s, 3H), 4.13 (m, 1H), 4.25 (d, 1H).

EXAMPLE 2

Preparation of 6,6-dimethoxy-5-hydroxy-3-oxo-tert-butyl Hexanoate

At 0° C., 6.6 g (165 mmol) of sodium hydride (55–60% in mineral oil) in 400 ml of tetrahydrofuran were initially charged in a 1000 ml double-jacketed flask. Using a dropping funnel, 23.75 g (150 mmol) of tert-butyl acetoacetate were subsequently added to the sodium hydride suspension over a period of 15 min (evolution of hydrogen). Stirring was continued for 60 min and, at 0° C., 100 ml of n-BuLi solution (1.6 M solution in hexane, 160 mmol) were then added dropwise to the reaction mixture over a period of approximately 40 min. Stirring was continued for about 25 min, and 34.7 g (150 mmol) of glyoxal 1,1-dimethyl acetal (45% strength solution in TBME) were subsequently added dropwise to the reaction mixture over a period of 30 min. Stirring was continued at 0° C. for 20 min and at 20° C. for 1 h. At 0° C., the reaction was quenched using 37 ml of concentrated HCl and 250 ml of water (>pH 8). The mixture was extracted twice with in each case 250 ml of diethyl ether. The crude product obtained by concentrating the organic phases was purified by column chromatography. In this manner, the desired compound was isolated in pure form.

(Yield: 17.3 g, 44%)

EXAMPLE 3

Preparation of 3-N-pyrrolidino-tert-butyl but-2-enoate

A solution of tert-butyl acetoacetate (7.91 g, 50 mmol) in 50 ml of toluene is admixed with 3.75 g of pyrrolidine (52.5 mmol) and refluxed on a water separator for 1.5 h. After this time, the theoretical amount of water has separated off. The enamine can be obtained in virtually quantitative yield by concentrating the reaction mixture.

$^1$H NMR (400 MHz, CDCl$_3$): 1.46 (s, 9H)

1.91 (m, 4H), 2.43 (s, 3H), 3.27 (brd. s, 4H), 4.41 (s, 1H).

What is claimed is:

1. A process for preparing a 6,6-dialkoxy-5-hydroxy-3-oxo-hexanoic acid ester of formula:

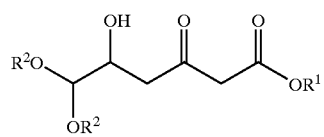

I in which R$^1$ and R$^2$ are identical or different and are C$_{1-6}$-alkyl, comprising reacting an alkyl acetoacetate of formula:

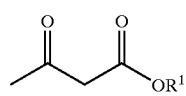

II in which R$^1$ is a defined above, in the presence of a base with an aldehyde of formula:

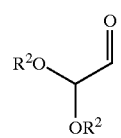

III in which R$^2$ is as defined above.

2. The process according to claim 1, wherein the reaction is carried out in an organic solvent in the substantial absence of water.

3. The process according to claim 2, wherein the reaction is carried out at a temperature of from −80° to 130° C.

4. The process according to claim 3, wherein a base is used which is capable of forming the dianion of the alkyl acetoacetate of formula II.

5. The process according to claim 4, wherein initially a deprotonation at the —CH$_2$— function of the alkyl acetoacetate of formula II is effected using a relatively weak base, and the dianion is formed only afterwards using a relatively strong base.

6. The process according to claim 1, wherein a base is used which is capable of forming the dianion of the alkyl acetoacetate of formula II.

* * * * *